(12) United States Patent
Rooks

(10) Patent No.: US 10,631,838 B2
(45) Date of Patent: Apr. 28, 2020

(54) DEVICES, SYSTEMS, AND METHODS FOR LOCATING PRESSURE SENSITIVE CRITICAL STRUCTURES

(71) Applicant: COVIDIEN LP, Mansfield, MA (US)

(72) Inventor: Kathy E. Rooks, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 987 days.

(21) Appl. No.: 15/144,945

(22) Filed: May 3, 2016

(65) Prior Publication Data
US 2017/0319190 A1    Nov. 9, 2017

(51) Int. Cl.
| A61B 17/00 | (2006.01) |
| A61B 5/00 | (2006.01) |
| A61B 8/12 | (2006.01) |
| A61B 90/00 | (2016.01) |
| A61B 8/00 | (2006.01) |

(52) U.S. Cl.
CPC ...... *A61B 17/00234* (2013.01); *A61B 5/0053* (2013.01); *A61B 5/442* (2013.01); *A61B 8/12* (2013.01); *A61B 90/03* (2016.02); *A61B 5/0048* (2013.01); *A61B 8/445* (2013.01); *A61B 2017/00106* (2013.01); *A61B 2017/00292* (2013.01); *A61B 2017/00367* (2013.01); *A61B 2090/032* (2016.02); *A61B 2090/065* (2016.02); *A61B 2090/08021* (2016.02); *A61B 2562/164* (2013.01)

(58) Field of Classification Search
CPC . A61B 17/00234; A61B 90/03; A61B 5/0053; A61B 5/442; A61B 8/12; A61B 8/085; A61B 8/4254; A61B 8/4466; A61B 8/485; A61B 2090/065
See application file for complete search history.

(56) References Cited

U.S. PATENT DOCUMENTS

| 5,398,689 A | * | 3/1995 | Connor | A61B 8/12 600/459 |
| 5,680,863 A | * | 10/1997 | Hossack | A61B 8/12 600/437 |

(Continued)

FOREIGN PATENT DOCUMENTS

| WO | 02/085214 A1 | 10/2002 |
| WO | 03/063698 A1 | 8/2003 |

(Continued)

OTHER PUBLICATIONS

Canadian Office Action issued in Appl. No. 2,965,951 dated Feb. 26, 2018 (3 pages).

(Continued)

*Primary Examiner* — Carolyn A Pehlke

(57) ABSTRACT

The present disclosure relates to devices, systems, and methods for controlling the pressure a sensor applies on the surface of tissue to facilitate locating underlying pressure sensitive critical structures. The laparoscopic device includes a handle and a shaft extending distally from the handle. A flexible member is slidably disposed within the shaft and movable between a retracted position and an extended position. A sensor is coupled to a distal end of the flexible member. The flexible member is configured to flex to limit an amount of pressure applied by the sensor to a tissue surface when the sensor is in contact with a tissue surface.

12 Claims, 3 Drawing Sheets

(56) References Cited

U.S. PATENT DOCUMENTS

| | | | |
|---|---|---|---|
| 5,957,849 A | 9/1999 | Munro | |
| 5,991,697 A | 11/1999 | Nelson et al. | |
| 6,006,127 A | 12/1999 | Van Der Brug et al. | |
| 6,383,141 B1* | 5/2002 | Itoi | A61B 8/12 600/459 |
| 6,551,302 B1* | 4/2003 | Rosinko | A61M 25/0084 604/22 |
| 6,569,098 B2 | 5/2003 | Kawchuk | |
| 6,837,855 B1 | 1/2005 | Puech | |
| 6,889,075 B2 | 5/2005 | Marchitto et al. | |
| 7,615,015 B2 | 11/2009 | Coleman | |
| 7,706,882 B2 | 4/2010 | Francischelli et al. | |
| 7,917,312 B2 | 3/2011 | Wang et al. | |
| 7,967,742 B2 | 6/2011 | Hoeg et al. | |
| 8,183,745 B2 | 5/2012 | Trolier-McKinstry et al. | |
| 9,375,196 B2 | 6/2016 | Zheng et al. | |
| 2004/0221853 A1 | 11/2004 | Miller | |
| 2005/0137501 A1 | 6/2005 | Euteneuer et al. | |
| 2005/0143662 A1 | 6/2005 | Marchitto et al. | |
| 2005/0217381 A1 | 10/2005 | Falk | |
| 2006/0036162 A1 | 2/2006 | Shahidi et al. | |
| 2006/0184042 A1 | 8/2006 | Wang et al. | |
| 2006/0278248 A1 | 12/2006 | Viswanathan | |
| 2007/0179380 A1* | 8/2007 | Grossman | A61B 5/0073 600/462 |
| 2007/0239007 A1 | 10/2007 | Silverman et al. | |
| 2009/0088634 A1 | 4/2009 | Zhao et al. | |
| 2009/0216129 A1 | 8/2009 | Lasser et al. | |
| 2009/0248007 A1* | 10/2009 | Falkenstein | A61B 18/1445 606/33 |
| 2009/0287223 A1 | 11/2009 | Pua et al. | |
| 2009/0318756 A1 | 12/2009 | Fisher et al. | |
| 2010/0217117 A1 | 8/2010 | Glossop et al. | |
| 2011/0106052 A1 | 5/2011 | Chiang et al. | |
| 2011/0230710 A1 | 9/2011 | Hoeg et al. | |
| 2012/0010506 A1 | 1/2012 | Ullrich | |
| 2012/0035474 A1* | 2/2012 | Deckman | A61B 8/0833 600/439 |
| 2012/0071757 A1 | 3/2012 | Salcudean et al. | |
| 2012/0136242 A1 | 5/2012 | Qi et al. | |
| 2013/0018281 A1 | 1/2013 | Nagale et al. | |
| 2013/0172786 A1 | 7/2013 | Olson et al. | |
| 2013/0218024 A1 | 8/2013 | Boctor et al. | |

FOREIGN PATENT DOCUMENTS

| | | |
|---|---|---|
| WO | 2007/066300 A2 | 6/2007 |
| WO | 2008017051 A2 | 2/2008 |
| WO | 2010/129773 A1 | 11/2010 |
| WO | 2012066446 A1 | 5/2012 |

OTHER PUBLICATIONS

Extended European Search Report dated Oct. 9, 2017 in European Application No. 17169233.8, 10 pages.

Austalian Examination Report issued in Appl. No. AU 2017202575 dated Sep. 11, 2018 (3 pages).

* cited by examiner

DEVICES, SYSTEMS, AND METHODS FOR LOCATING PRESSURE SENSITIVE CRITICAL STRUCTURES

BACKGROUND

1. Technical Field

The present disclosure relates generally to locating pressure sensitive critical structures. More particularly, the present disclosure relates to devices, systems, and methods for controlling the pressure a sensor applies on the surface of tissue to facilitate locating underlying pressure sensitive critical structures.

2. Background of Related Art

Recent developments in medical technologies have led to an increase in the prevalence of minimally-invasive surgical procedures. Prior to these advances, surgical procedures were often painful, required large incisions, resulted in large wounds and scars, and involved prolonged procedure and recovery times. Advances in minimally-invasive technologies, specifically laparoscopic surgery, now permit many of these procedures to be performed with smaller incisions, reduced healing times, and reduced trauma to a patient.

However, laparoscopic procedures require surgeons to interact with tissue with tools rather than manipulate tissue with their hands. This leads to a reduction in the amount of tactile feedback available to a surgeon and limits a surgeon's ability to gauge the amount of pressure applied to tissue. The lack of tactile feedback makes it difficult to use sensing technologies to identify pressure sensitive structures or locate structures without compromising the structure and/or the ability to detect it.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

In accordance with the present disclosure, a laparoscopic device for controlling the pressure a sensor applies on the surface of tissue to facilitate locating underlying pressure sensitive critical structures is provided. The laparoscopic device comprises a handle, a shaft extending distally from the handle, a flexible member slidably disposed within the shaft and movable relative thereto between a retracted position and an extended position, and a sensor coupled to a distal end of the flexible member. The sensor is oriented perpendicularly relative to a longitudinal axis defined by the shaft in at least the extended position of the flexible member. The flexible member is configured to flex to limit an amount of pressure applied by the sensor to a tissue surface.

The laparoscopic device according may include a distal tip configured to receive the sensor when the flexible member is in the retracted position. In one aspect of the disclosure, the distal tip is coupled to the shaft. In a further aspect the laparoscopic device includes a rod disposed within the shaft, wherein the distal tip is coupled to the rod. Still further, the flexible member may be formed in an arcuate shape which resists flexure normal to its longitudinal axis.

The distal tip may further include a chamfer feature configured to orient the sensor at a pre-determined angle when the flexible member is disposed in the retracted position. The pre-determined angle may be for example 30 degrees, 60 degrees, or 90 degrees.

In a further aspect the flexible member is a flexible circuit and the sensor is integrated into the flexible circuit.

In yet another aspect of the disclosure the handle includes a slide knob configured to extend or retract the flexible member. The handle may further include a rotation dial configured to rotate the flexible member relative to the handle. Still further the handle may include an activation button configured to activate the sensor. And the sensor may be an ultrasound transducer.

A method for locating critical structures is also provided in accordance with the present disclosure. The method comprises extending a flexible member having a sensor towards a distal end thereof distally from a shaft, wherein, in an at-rest position of the flexible member, the sensor is oriented perpendicularly relative to a longitudinal axis of the shaft. The method further comprises placing the sensor on a tissue surface, and applying pressure towards the tissue surface causing the flexible member to deflect from the at-rest position to thereby limit a pressure applied to the tissue surface. The method may further comprise activating the sensor to sense an underlying critical structure.

BRIEF DESCRIPTION OF THE DRAWINGS

Various aspects and features of the present disclosure are described herein with reference to the drawings wherein.

DETAILED DESCRIPTION

Particular embodiments of the present disclosure are described below with reference to the accompanying drawings.

Figure 1:
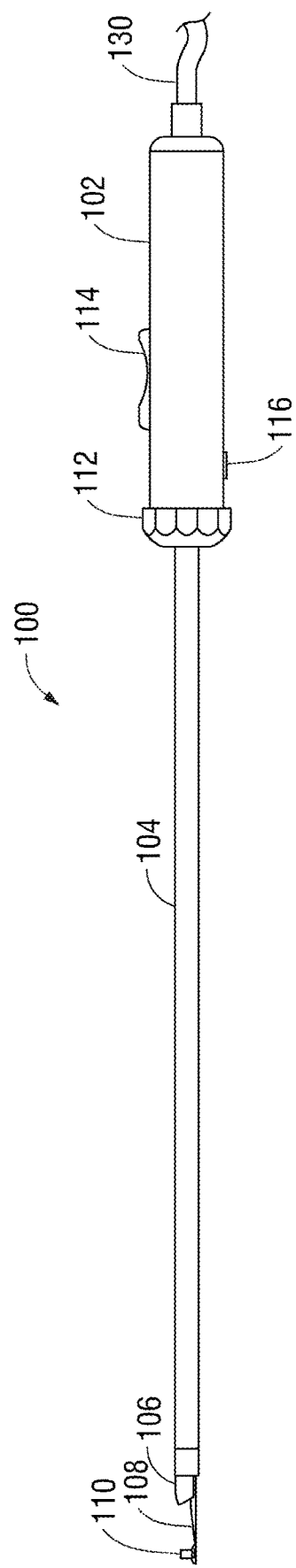
FIG. 1 is a side view of a laparoscopic device for locating pressure sensitive critical structures provided in accordance with the present disclosure.

FIG. 1 depicts a laparoscopic device 100 configured to facilitate locating underlying pressure sensitive critical structures. Laparoscopic device 100 includes a handle 102, a shaft 104 extending distally from the handle 102, a distal tip 106 may be coupled to the shaft 104, a flexible member 108 extending through and distally from the shaft 104, and a sensor 110 disposed towards a distal end of the flexible member 108. For the purposes herein, the laparoscopic device 100 is detailed as a stand-alone device; however, the flexible member 108 and sensor 110 may alternatively be incorporated into any one of a variety of laparoscopic tools including ultrasonic dissectors, bipolar forceps, surgical staplers, endoscopes, etc. Further, although the embodiments described below reference sensor 110 as an ultrasound sensor including an ultrasound transducer 118 (FIGS. 2A and 2B), it is contemplated that sensor 110 can be any of a number of different types of sensors. For example, sensor 110 may be an ultrasound sensor (as described below), an optical sensor, a pressure sensor, or other suitable sensor.

Handle 102 includes a variety of controls including a rotation dial 112, a slide knob 114, and an activation button 116. Rotation dial 112 allows for the rotation of the shaft 104 and/or the flexible member 108 relative to handle 102. In certain embodiments it may be desirable to employ a rod 120 (FIGS. 3A and 3B) within the shaft 104 and the distal tip 106 may be formed on a distal portion of the rod 120. In such embodiments rotation dial 112 can cause the rod 120 to rotate separately or in addition to rotation of the shaft 104. Slide knob 114 allows for the extension and/or retraction of the flexible member 108 relative to the distal end of the shaft 104 and the distal tip 106. Activation button 116 activates or deactivates the sensor 110. The handle 102 further includes a cable 130 adapted to connect to a source of energy for powering the sensor 110, although the laparoscopic device 100 may alternatively be configured as a battery-powered device having a battery (not shown) disposed within the handle 102. The cable 130 may additionally or alternatively be configured to couple to an external computer and/or display for processing and/or displaying the information sensed by sensor 110.

Figure 2A:
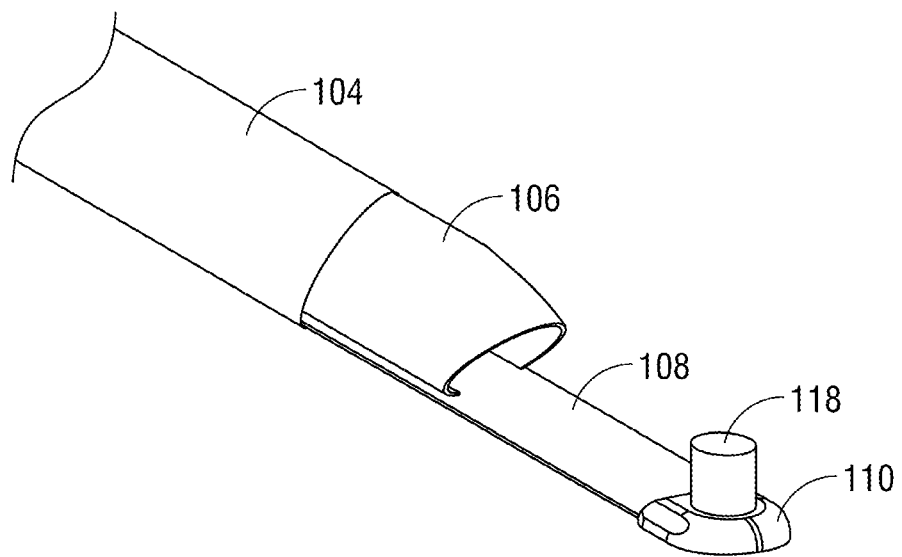
FIG. 2A is an enlarged, perspective view of a distal end of the laparoscopic device of FIG. 1, disposed in an extended, at-rest position.

FIG. 2A depicts an enlarged view of the distal end of the laparoscopic device 100. In particular, FIG. 2A shows the flexible member 108 disposed in an extended, at-rest position, wherein the flexible member 108 extends distally from the distal tip 106. Flexible member 108 may be retracted to a retracted position, wherein the distal end of flexible member 108 is disposed at least partially within distal tip 106 and/or shaft 104, via manipulation of slide knob 114 (FIG. 1). As noted above, flexible member 108 extends through the shaft 104 and exits through the distal end of the shaft 104. At its proximal end, the flexible member 108 extends into handle 102 and operably couples to slide knob 114 (FIG. 1). The flexible member 108 may be formed in an arcuate shape which resists flexure of the flexible member 108 normal to its longitudinal axis. In certain embodiments the flexible member 108 may wrap partially or fold around an internal rod 120 (FIGS. 3A and 3B) disposed in the shaft 104, or simply disposed in the arcuate shape in the shaft 104. In embodiments where so provided, wrapping or folding the flexible member 108 about the internal rod 120 creates an arc in the flexible member 108. This arc improves the structural support and area moment of inertia of the flexible member 108. The flexible member 108 may be formed of a flex circuit. In particular, flexible member 108 may include a double layer circuit including a polyimide base coated with a layer of copper. The polyimide base may have a thickness of 1.0 mil and the copper may be ½ oz of copper. The total thickness of the flexible member may range from 6 to 12 mils. However, other configurations are also contemplated.

The sensor 110, as noted above, is disposed towards the distal end of the flexible member 108. In an embodiment, the sensor 110 may be electrically coupled to the flexible member 108. As previously noted, in one embodiment, sensor 110 is an ultrasound sensor and includes an ultrasound transducer 118. In this embodiment, ultrasound transducer 118 may consist of either a single element to enable one-dimensional imaging, or alternatively, ultrasound transducer 118 may consist of an array for two-dimensional imaging. As described in more detail below with reference to FIGS. 4A and 4B, sensor 110 and transducer 118 may be either assembled on the flexible member 108 (FIG. 4A) or integrated into the flexible member 108 (FIG. 4B) during the manufacturing of the flexible member 108. In an embodiment, the sensor 110, including the ultrasound transducer 118, is positioned relative to the flexible member 108 such that the sensor 110 is substantially perpendicular to a longitudinal axis of the flexible member 108 and a longitudinal axis of shaft 104, in an at-rest position of the flexible member 108. More specifically, the sensor 110 may be oriented such that the directions of ultrasound signal transmission from and/or reception by the sensor 110 are substantially perpendicular to the longitudinal axis of the flexible member 108 and the longitudinal axis of shaft 104 in an at-rest position of the flexible member 108.

With continued reference to FIG. 2A, the distal tip 106 is disposed at the distal end of shaft 104. The distal tip 106 is configured to house at least a portion of the sensor 110 and/or at least a portion of the distal end of the flexible member 108 when the flexible member 108 is disposed in the retracted position. The distal tip 106 thereby protects the sensor 110 (including the ultrasound transducer 118) when in the retracted position and allows the laparoscopic device 100, including the sensor 110, to pass through laparoscopic ports safely. In an embodiment, the distal tip 106 is coupled to the distal end of shaft 104, while in yet another embodiment, the distal tip 106 is coupled to a distal end of rod 120 (FIGS. 3A and 3B), which extends through shaft 104.

Figure 2B:
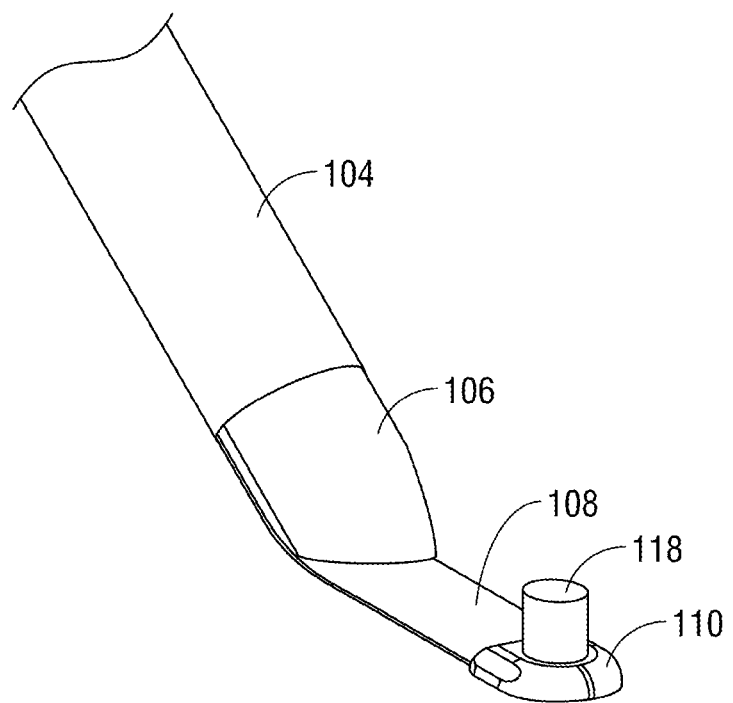
FIG. 2B is an enlarged, perspective view of the distal end of the laparoscopic device of FIG. 1, disposed in an extended, flexed position.

FIG. 2B depicts the flexible member 108 in a flexed position, when the sensor 110 is placed on a surface and pressure is applied. In this manner, the flexible member 108 acts as a cantilever-beam or spring that controls the amount of pressure applied to the surface. That is, as additional pressure is applied, rather than imparting that pressure onto the surface, the flexible member 108 flexes or deflects from the at-rest position (or flexes further), thereby inhibiting application of additional pressure to the surface. In an embodiment, the flexible member 108 is used as the transmission line, e.g., a flex circuit, to electrically couple the sensor 110 to the handle 102 (FIG. 1).

Referring generally to FIGS. 1-2B, in a number of laparoscopic applications, it is important to control and/or limit the amount of pressure applied to the surface of tissue. In particular, it is important to control the amount of pressure exerted by laparoscopic devices on pressure sensitive tissue such as the ureter and bile duct. The ureter, for example, is a lumen made of smooth muscle fibers that propel urine from the kidney to the bladder through peristalsis. However, ureter walls are not as rigid as blood vessels and thus, can be easily compressed when pressure is applied to the walls. When the ureter is close to the surface of the peritoneum, the amount of force needed to compress the ureter is very small. Specifically, it has been found that compression of the ureter may require as little as 0.005-0.050 lbs of force. These low forces make it difficult to place a sensor on tissue near the ureter without compressing the ureter. When the ureter walls are collapsed, all the urine is pushed out of the ureter and the anechoic space is eliminated. Without the presence of urine in the ureter (and an anechoic space), an ultrasound sensor cannot detect the ureter structure. In such instances, ultrasound sensors may provide false negative results as to the presence of the ureter. As noted above, the flexible member 108 is configured to flex to limit the contact pressure applied by the sensor 110 to tissue, thus inhibiting collapse of the ureter walls and enabling detection of the ureter.

The mechanical properties of the flexible member 108 control the maximum contact pressure applied from the sensor 110 to tissue. The exact deflection load of the flexible member 108 varies as at least as a function of the thickness of the flexible member 108, and the distance that the flexible member 108 is extended distally past the distal tip 106. In particular, deflection load increases as the thickness of the flexible member 108 increases, or when the distance that the flexible member 108 is extended distally past the distal tip 106 decreases. As such, with these parameters in mind, the flexible member 108 may be configured to achieve a particular deflection load corresponding to the desired maximum contact pressure applied from the sensor 110 to tissue.

In use, a clinician inserts the laparoscopic device 100 into a patient towards a target site, for example, a site where it is desired to sense for critical structures. When the laparoscopic device 100 is initially inserted into the patient, the flexible member 108 is in the retracted position. In particular, the flexible member 108 is retracted so that the sensor 110 is at least partially housed within and protected by the distal tip 106. When the distal tip 106 is located near the target site, the clinician uses the slide knob 114 to extend the flexible member 108 and the rotation dial 112 to orient the flexible member 108 to place the sensor 110 on the surface of the target tissue. Once properly positioned, the clinician can activate sensor 110 by engaging activation switch 116. As previously described, the configuration of the flexible member 108 allows the clinician to apply a limited and consistent contact pressure on the tissue surface, regardless of whether the laparoscopic device 100 is manipulated further towards the tissue surface.

Figure 3A:
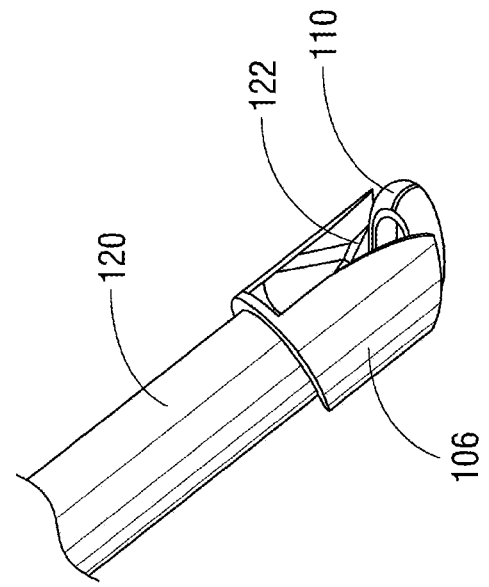
FIG. 3A is an enlarged, perspective view of the distal end of another laparoscopic device for locating pressure sensitive critical structures provided in accordance with the present disclosure, disposed in an extended position.
Figure 3B:
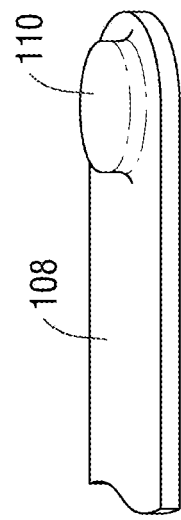
FIG. 3B is an enlarged, perspective view of the distal end of the laparoscopic device of FIG. 3A, disposed in a retracted position.

FIGS. 3A and 3B depict another embodiment of a laparoscopic device similar to laparoscopic device 100 (FIG. 1), except for the configuration of the distal tip 106. Thus, only these differences will be detailed below. The distal tip 106 is configured to receive and house the sensor 110. In this embodiment, the distal tip 106 is coupled to the distal end of rod 120. Rod 120 extends through shaft 104 (FIG. 1; not shown in FIGS. 3A and 3B).

The inner surface of distal tip 106 includes a chamfer feature 122. When the flexible member 108 is extended (FIG. 3A), the broad surface of the flexible member 108 and the sensor 110 are oriented perpendicular to the longitudinal axis of the rod 120 (and shaft 104 (FIG. 1), allowing the flexible member 108 to function similarly as detailed above. However, when the flexible member 108 is retracted (FIG. 3B), the chamfer feature 122 serves as a guide track that urges the sensor 110 to an angled orientation in accordance with the angle of the chamfer feature 122. The angle of the chamfer may range from 30° to 90°, may be 30°, 60°, or 90°, or may define another suitable angle, when measured from a longitudinal axis of the shaft 104. The angled chamfer feature 122 allows the clinician maintain the orientation of the sensor 110 and the ability to collect data with the sensor even in the retracted position, whereas this functionality would be limited if the sensor 110 were retracted into the shaft 104. Additionally, when the sensor is fully retracted (FIG. 3B), the rigid nature of the shaft 104 gives the clinician increased tactile feedback from the sensor 104 when placed on a surface, and allows use in situations where the tissue to be detected is not as pressure sensitive, for example, when sensor 110 is utilized to detect blood flow through a blood vessel using Doppler.

Figure 4A:
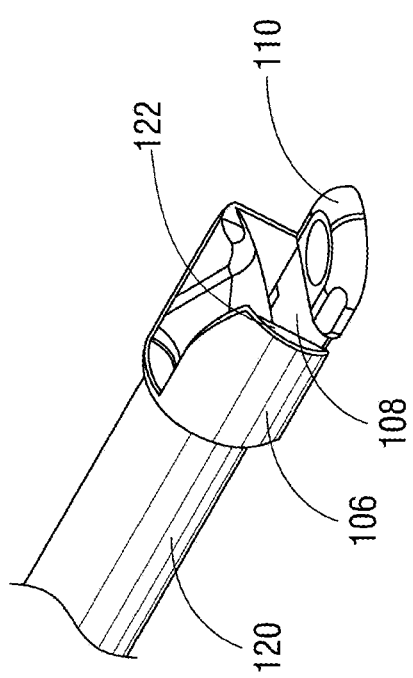
FIG. 4A is an exploded, perspective view of one configuration of a flexible member provided in accordance with the present disclosure and configured for use with the device of FIG. 1, the device of FIG. 3A, or any other suitable device.
Figure 4B:
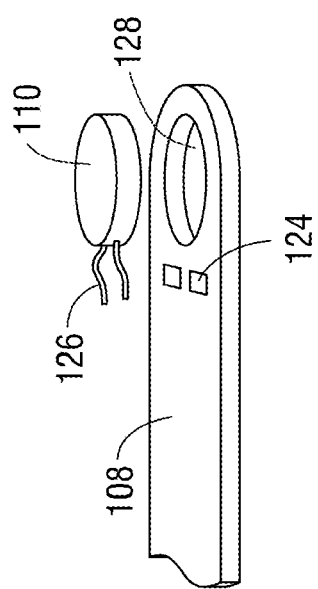
FIG. 4B is a perspective view of another configuration of a flexible member provided in accordance with the present disclosure and configured for use with the device of FIG. 1, the device of FIG. 3A, or any other suitable device.

FIGS. 4A and 4B depict two configurations which may be utilized for engaging the flexible member 108 and the sensor 110. In the configuration of FIG. 4A, the flexible member 108 and the sensor 110 are assembled. In particular, the sensor 110 is seated within an aperture 128 defined at least partially through the flexible member 108 towards the distal end thereof. The flexible member 108 also contains electrical terminals 124 configured to electrically couple to wires 126 of sensor 110. The electrical terminals 124 of the flexible member 108 may be coupled to circuit traces extending through the flexible member 108 (in configurations where the flexible member 108 is configured as a flex circuit), may be coupled to wires extending through the flexible member 108, or may define another suitable configuration. In either configuration, the electrical terminals 124 are configured to couple to a power source and/or computer (e.g., via the cable 130 (FIG. 1)) in order to power the sensor 110 and/or process the signals received from the sensor 110, respectively.

As an alternative to the configuration of FIG. 4A, the sensor 110 may be integrated into the flexible member 108 during the manufacturing process, as depicted in FIG. 4B. In this configuration, the sensor 110 is potted into the flexible member 108 during manufacturing and electrically coupled therewith.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A laparoscopic device comprising:
a handle;
a shaft extending distally from the handle, the shaft defining a longitudinal axis;
a flexible member slidably disposed within the shaft and longitudinally movable relative thereto between a retracted position, where a distal portion of the flexible member is disposed at least partially within the shaft, and an extended position, where the distal portion of the flexible member extends distally from a distal end of the shaft; and
a sensor coupled to the flexible member,
wherein the flexible member is configured to bend upon application of pressure thereto to limit an amount of pressure applied by the laparoscopic device against tissue.

2. The laparoscopic device according to claim 1, further comprising a distal tip configured to receive the sensor when the flexible member is in the retracted position.

3. The laparoscopic device according to claim 2, further comprising a rod disposed within the shaft, wherein the distal tip is coupled to the rod.

4. The laparoscopic device according to claim 2, wherein the distal tip further comprises a chamfer feature configured to orient the sensor at a pre-determined angle when the flexible member is disposed in the retracted position.

5. The laparoscopic device according to claim 4, wherein the pre-determined angle is 30 degrees, 60 degrees, or 90 degrees.

6. The laparoscopic device according to claim 1, wherein the flexible member is a flexible circuit.

7. The laparoscopic device according to claim 6, wherein the sensor is integrated into the flexible circuit.

8. The laparoscopic device according to claim 1, wherein the handle includes a slide knob configured to extend or retract the flexible member.

9. The laparoscopic device according to claim 1, wherein the handle includes a rotation dial configured to rotate the flexible member relative to the handle.

10. The laparoscopic device according to claim 1, wherein the handle includes an activation button configured to activate the sensor.

11. The laparoscopic device according to claim 1, wherein the sensor includes an ultrasound transducer.

12. The laparoscopic device according to claim 1, wherein the flexible member is configured to transition from a linear condition to a bent condition upon application of pressure to the flexible member.

* * * * *